United States Patent [19]

Chaudhary et al.

[11] 4,026,928
[45] May 31, 1977

[54] LOW MOLECULAR WEIGHT VINYL POLYMERS AND PROCESS FOR PREPARING

[75] Inventors: Sohan S. Chaudhary, Monroeville, Pa.; Edward M. Fettes, Oak Brook, Ill.

[73] Assignee: ARCO Polymers, Inc., Philadelphia, Pa.

[22] Filed: Oct. 27, 1970

[21] Appl. No.: 84,526

[52] U.S. Cl. .................. 260/515 A; 260/515 P; 260/523 R; 260/61; 260/635 R; 260/75 T
[51] Int. Cl.² .................................. C07C 63/56
[58] Field of Search ........ 260/515 A, 515 P, 523 R

[56] References Cited
UNITED STATES PATENTS

| | | | |
|---|---|---|---|
| 3,108,994 | 10/1963 | Zelinski et al. | 260/515 |
| 3,135,716 | 6/1964 | Uraneck et al. | 260/45.5 |
| 3,235,589 | 2/1966 | Berenbaum et al. | 260/533 |

Primary Examiner—Anton H. Sutto
Attorney, Agent, or Firm—Synnestvedt and Lechner

[57] ABSTRACT

Novel low molecular weight vinyl polymers with chain terminating reactive groups and methods for their preparation are disclosed in which the low molecular weight polymers may be represented by the formula

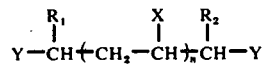

in which
Y is

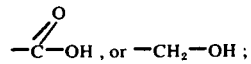

$R_1$ is hydrogen, lower alkyl having 1 to 4 carbon atoms, or halogen;
$R_2$ is hydrogen, lower alkyl having 1 to 4 carbon atoms, or halogen;
X is halogen or aryl, or alkyl groups free from ethylenic unsaturation and hydroxyl groups; and
n is from 5 to 50.

These low molecular weight vinyl polymers are useful as prepolymers or precursors in the formation of novel species of certain types of high polymers such as, for example, of the polyester, polyurethane, polyurea, polyepoxy or polyamide types. The low molecular weight vinyls of this invention also have utility, for example, as plasticizers and lubricants.

Synthesis of the low molecular weight vinyl polymers includes the steps of copolymerizing a major amount of a vinyl monomer with a minor amount of a diene monomer; ozonizing the resulting copolymer to cleave the polymeric chain at each point of ethylenic unsaturation; and changing the state of oxidation of the end groups of the resulting chain segments to provide reactive end groups at each end of their ends.

4 Claims, No Drawings

LOW MOLECULAR WEIGHT VINYL POLYMERS AND PROCESS FOR PREPARING

BACKGROUND OF THE INVENTION

This invention relates to aliphatic dibasic acids and aliphatic glycols. More particularly, this invention relates to low molecular weight vinyl polymers with chain terminating reactive carboxyl or hydroxyl groups, methods for their preparation, and high polymers that can be made therefrom.

Aliphatic dibasic acids and aliphatic glycols are extremely important groups of industrial chemicals. They are used for many purposes, such as plasticizers and lubricants, and of even greater importance is their use as monomers in the preparation of high polymers. With respect to their use as monomers in polymerization processes, these materials are extremely versatile and may be used in the formation of a large number of condensation polymers. By way of example of some of the more commercially significant condensation polymers that may be so formed are the polyesters which can readily be prepared from the reaction between the dibasic acids and glycols themselves; polyamides which can be prepared through the reaction of a dibasic acid with a diamine; polyurethanes and polyureas which can be prepared by the reaction of a dihydric alcohol with diisocyanates; and polyepoxies that can be prepared by the reaction of an epoxy either with a dibasic acid or a dihydric alcohol.

It is, of course, apparent that, as these difunctional monomers become an internal part of the polymeric chain, various physical and chemical properties of the high polymer will be innfluenced by the structure of the difunctional monomer. For example, the structure of the difunctional monomeric compounds may have significant effects in determining the extent and nature of the crystalline and amorphous regions within the polymer. This, in turn, can significantly affect physical and rheological properties of the polymer such as strength, impact, moisture absorption, elongation, elasticity, cold flow, heat distortion temperature, low temperature embrittlement, dielectric properties, etc., etc.

While a number of difunctional compounds of the subject type are theoretically available for use as monomers, in point of fact, only comparatively few find significant commercial utilization in the preparation of high polymers, variously because the vast majority of these difunctional compounds may not be readily available, they may be hard to synthesize, or they may be comparatively expensive as compared with other difunctional materials that are capable of producing equivalent or better combinations of properties.

SUMMARY OF THE INVENTION

Accordingly, it is an object of this invention to provide new and useful aliphatic dibasic acids and aliphatic glycols and methods for their preparation.

Another object of this invention is to provide low molecular weight polymers with reactive terminal groups that may be used as precursors in the formation of high polymers.

Another object of this invention is to prepare novel low molecular weight polymers from readily available monomeric materials for use as precursors in the formation of high polymers.

Another object of this invention is to provide polymers having improved physical properties using the low molecular weight polymers of this invention.

Briefly, these and other objects of this invention are achieved by copolymerizing a major amount of a vinyl with a minor amount of a diene; ozonizing the resulting copolymer to cleave the polymeric chain at each point of ethylenic unsaturation; changing the state of oxidation of the end groups of the resulting chain segments to provide reactive end groups at each end of the chain segments; and preparing high polymers by condensation reactions between the chain segments having reactive end groups and other monomers.

PREPARATION OF THE LOW MOLECULAR WEIGHT VINYL POLYMERS

In preparing the low molecular weight vinyl polymers of the present invention, a major molar quantity of a vinyl monomer is copolymerized with a minor molar quantity of a diene monomer. For convenience and clarity of description, reference generally will be made to styrene as the vinyl and butadiene as the diene. These specific materials were chosen as being particularly illustrative of the invention due to the ease with which they can be copolymerized, their ready availability, their comparative inexpensiveness, and the good combination of properties that they impart to certain high polymers. It is to be understood that the invention is not intended to be so limited since a number of other suitable vinyl and diene compounds are useful in the practice of the instant invention and, from the following description, will readily suggest themselves to those skilled in the art.

Generally, the free radical copolymerization of styrene and butadiene will proceed as follows (the initiation step is not shown):

$$n(CH_2=CH) + CH_2=CH-CH=CH_2 \longrightarrow \quad 1.$$

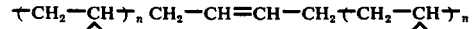

It can be seen that a number of polystyrene groups are formed that are joined together by intermediate butadiene groups. The number of recurring units in the polystyrene groups is determined by the relative proportions of the butadiene and styrene monomers: the higher the ratio of styrene monomer to butadiene monomer, the greater will be the number of recurring units in the polystyrene groups of the copolymer. By way of example, it has been calculated on a statistical basis that a segment having an average sequence length of about 10 styrene units will be obtained from the copolymerization of about 93 parts of styrene with 7 parts of butadiene. (Here and elsewhere in the specification, examples and claims, unless otherwise indicated, all parts are given by weight.)

The above free radical polymerization may be carried out by utilizing any conventional initiator, provided that it does not give rise to unwanted end groups terminating the polymer chain. As a practical matter, however, if the copolymer is polymerized to a high molecular weight, the terminal groups on the copolymer will tend to be relatively insignificant.

The copolymerization can conveniently be conducted either as a suspension or emulsion polymerization.

A feature of the styrene-butadiene copolymer formed in accordance with Equation 1 is that the butadiene linkage between the polystyrene groups contains one point of ethylenic unsaturation. By attacking the polymeric chains at each of these unsaturated points, the polymeric chain can be cleaved to form a number of chain segments essentially comprised of a low molecular weight polystyrene group terminated by the residuum of the cleaved butadiene group.

After the copolymer has been prepared, it is dissolved in a solvent, such as chloroform, and is then contacted with ozone. As can be seen from Equation 2, the ozone attacks the points of ethylenic unsaturation to form an ozonide. The ozonide is, in turn, oxidized by any standard technique known to the art, such as by treatment with peracetic acid or hydrogen peroxide, to cleave the polymeric chain and oxidize the end groups to form carboxylic acid (Equation 3).

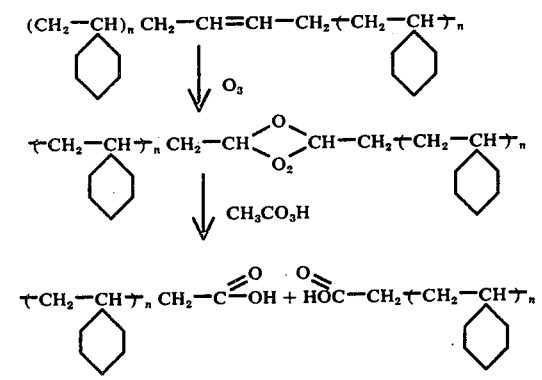

In addition to the formation of low molecular weight polystyrene terminated by carboxylic acid end groups, it is also possible to prepare similar low polymers that are terminated by hydroxyl end groups. The process of preparing these glycols is similar to that described above with respect to dibasic acids except that, after the ozonide is obtained, it is subjected to strongly reducing conditions rather than oxidation conditions. Treating the ozonide with a strong reducing agent — for example, lithium aluminum hydride or sodium borohydride — will cause the chain to cleave at the ozonide linkage and provide an active hydroxyl end groups at each end of the segment. The use of conventional catalytic reduction techniques may improve the yield.

In the foregoing discussion, it has been assumed that the butadiene is 1-3 butadiene, and that addition occurs through a 1-4 mechanism. A minor amount of 1-2 addition probably occurs giving rise to side chains which, in turn, when subjected to oxidizing or reducing conditions, will yield tri- and polybasic acids and tri- and polyhydric alcohols. For the most part, 1-2 addition is very minor in comparison to 1-4 addition and, for purposes herein, has been ignored.

THE VINYL MONOMERS

A fairly large latitude exists in the selection of the vinyl monomer, and generally the main requirement that need be met is that the vinyl is capable of copolymerizing with the diene, to a useful degree, at random in a chain. Additionally, the vinyl, after polymerization, should be free from ethylenic unsaturation that would provide reactive sites for ozone. It would also be undesirable to select a vinyl monomer having hydroxyl groups. No attempt has here been made to compile a comprehensive list of various vinyls that may be used in this invention since the list is voluminous, the vinyls are well known to those skilled in the art, and they may be found in standard texts such as, for example, Copolymerization, edited by G. E. Ham, Interscience Publishers, New York, New York, pages 713–717, where a number of vinyls are given that copolymerize with butadiene. As elsewhere noted, the vinyl used will influence the properties of the low molecular weight polymer as well as any high polymers prepared therefrom.

THE DIENE MONOMERS

The selection of the diene monomer for use in this invention is somewhat more limited than the vinyl. In addition to copolymerizing with the vinyl, the diene must be such that, after copolymerization, there should not be reactive sites for ozone except the olefinic carbon to carbon double bond as arises from a 1,3-diene rearrangement. Within this framework, dienes useful in this invention should be of the general type

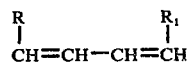

in which R and $R_1$ can be different or the same as each other and are selected from the group comprising:
hydrogen;
halogen (preferably chlorine); and
lower alkyl having 1 to 4 carbon atoms.

Examples of suitable dienes that meet these requirements are 1,3 butadiene; piperylene; 1,4 dimethyl-1,3 butadiene.

When a symmetrical diene, such as butadiene, is used as the diene monomer, cleavage of the chain will take place at the mid point of the butadiene group. As a result, each end of the polyvinyl segment will be terminated by identical groups that represent the product of oxidation of one-half of the butadiene (or other symmetrical diene) group. It follows that since there are two carbons in each half of the butadiene group, alkyl groups will be provided intermediate the polyvinyl group of the segment and the carboxylic acid end groups. This is desirable since, as a general rule, it can be predicted that the reactivity of the acid end groups of the segments will increase the further they are removed from proximity to the aryl groups of the polystyrene. For this reason it is believed that the reactivity of the acid end groups of these segments is improved by interposing at least one alkyl group between the reactive end groups and the polystyrene.

If it is not of great importance whether each end of the polyvinyl segment is the same, unsymmetrical dienes, such as piperylene, may be used.

THE POLYMERIC PRODUCTS

As previously mentioned, the difunctional low molecular weight polymers of this invention may be used in some instances as plasticizers and lubricants, and find particular utility in condensation reactions to form high polymers. The low molecular weight vinyl polymers terminated by carboxylic acid end groups can be reacted, for example, with glycols to form polyesters, with diamines to form polyamides, and with epoxies to form polyepoxies. The low molecular weight vinyl polymers terminated in hydroxyl end groups may be reacted, for example, with dibasic acids to form polyesters, with diisocyanates to form polyurethanes and polyureas, and with epoxies to form polyepoxies. Since the vinyl polymers become an integral part of the polymeric chain, the properties of the high polymer can be varied by varying the structure and number of recurring groups in the low molecular weight vinyl polymers. The structure of the recurring groups will be determined by the selection of the particular vinyl monomer that is copolymerized with the diene, the end groups will be determined by the selection of the diene that is copolymerized with the vinyl, and the number of recurring vinyl groups in the low molecular weight polymer will be determined by the ratio of the vinyl monomer to the diene monomer.

EXAMPLE I

An emulsion copolymerization was conducted by mixing the following materials in a reaction vessel:

|  | Parts |
|---|---|
| Styrene | 93 |
| Butadiene | 7 |
| Sodium lauryl sulfate (Sipex, 30% Sol.) | 3 |
| Sodium sulfoxylate formaldehyde (SFS, 4% Sol.) | 0.20 |
| t-Butyl hydroperoxide | 0.30 |
| Acetic acid (glacial) | 0.20 |
| Water | 152 |

A half-hour induction period was observed and, thereafter, the polymerization proceeded with a gradual build-up of viscosity. Overnight holding of the reaction product resulted in high conversions (94–95%). Recovery and subsequent air drying yielded a brittle and easily pulverizable copolymer. A very low amount of residual styrene monomer (less that 0.5%) was found in the vacuum-dried product.

Dilute (3–6%), rather viscous solutions were made in chloroform. Since chloroform is essentially unaffected by ozone, all subsequent processings (ozonolysis and oxidation) were carried out in this solvent.

The copolymer solution was charged into a flask, cooled to about −10° C, and ozone was introduced through a sintered disc entry tube at the bottom of the flask. Ozone was found to be quite reactive toward the olefinic unsaturation of the copolymer. The viscous character of the solution diminished as ozone was conducted through the reaction mixture. Some traces of ozone were detected in the effluent gas. To compensate for the slight loss, and to ensure full reaction of the butadiene unsaturation, a 15% excess of ozone was used. Further, to ensure a higher degree of contact, the ozonide material was allowed to stand overnight.

The contents of the flask were then refluxed using 2 moles of peracetic acid per mole of ozone and a small amount of glacial acetic acid. Addition of peracetic acid was made in 3-4 increments. in the beginning, the reaction mixture became turbid, but it attained clarity on refluxing. Excess of oxidizing agent was ensured even after 24 hours of refluxing.

Excess of peracetic acid, acetic acid and water-soluble components were washed off with several water washings until the aqueous portion showed the absence of peroxide. The vacuum-dried carboxylic acids had a faint smell like that of acetic acid and the solid was stirred with a large amount of water, filtered and re-dried as usual.

Alkali-soluble polystyrene carboxylic acids were recovered in yields of approximately 90% of theory. The carboxylic acids had number-average molecular weights of 1000 and were shown to have nearly two carboxylic acid groups per unit molecule. The hydrocarbon portion of the product carboxylic acids was essentially all polystyrene with only trace amounts of residual butadiene unsaturation.

EXAMPLE II

The following materials were mixed to carry out a styrene-butadiene suspension copolymerization:

|  | Parts |
|---|---|
| Styrene | 93 |
| Butadiene | 7 |
| Water | 100 |
| Benzoyl peroxide | 0.25 |
| t-Butyl peroxybenzoate | 0.06 |
| t-Dodecyl mercaptan | 0.15 |
| Polyvinyl alcohol | 0.20 |

The polymerization cycle was 10 hours at 100° C and 4 hours at 115° C. The resulting copolymer had a butadiene content of about 6.8%.

The copolymer was dissolved in chloroform, ozonized and oxidized as in Example I. The polystyrene dicarboxylic acid recovered was substantially the same as that of Example I above.

EXAMPLE III

The polystyrene dicarboxylic acid of Example I was reacted in varying proportions to form linear polyesters which were then cut and cured with either vinyl toluene or styrene monomers. The mole ratio of the reactants to form the linear polyesters were as listed in the following table:

Table 1

|  | Resins | | | |
|---|---|---|---|---|
|  | A | B | C | D |
| 1,4 cyclohexanedimethanol | 2 | 2 | 2 | — |
| neopentyl glycol | 2 | 2 | 2 | 4 |
| Δ⁴ tetrahydrophthalic anhydride | 1 | — | — | — |
| maleic anhydride | 2.7 | 3 | 3 | 3 |
| polystyrene dicarboxylic acid | 0.3 | 1 | 1 | 1 |

The resulting polyesters were then cut and cured as follows:

Resin A — 60 parts polyester with 40 parts vinyl toluene;

Resin B — 60 parts polyester with 40 parts vinyl toluene;

Resin C — 50 parts polyester with 50 parts vinyl toluene;

Resin D — 50 parts polyester with 50 parts styrene.

The following observations were made of the physical and chemical properties of the resins:

THERMAL STABILITY

The thermal stability of Resins A, B and C was measured and compared to a commercially available polyester resin selected for its known high thermal stability. (The commercial resin is sold under the trade designation V7000-15 by Koppers Company, Inc.) The thermal stability of Resins A, B and C (as measured by weight loss at elevated temperatures) compared favorably at 220° C with the commercial resin, and at 260° C Resins B and C showed considerably improved stability compared with the commercial resin. Resin C appeared slightly more stable then Resin B.

As Resin C appeared to have the greatest thermal stability, certain mechanical and electrical properties were checked of samples of the resin as cured with 1% benzoyl peroxide for 2 hours at 60° C, 1 hour at 75° C, and 2 hours at 135° C.

| Flexural strength | 15,300 psi |
|---|---|
| Flexural modulus | 442,000 psi |
| Tensile strength | 8,400 psi |
| Tensile modulus | 440,000 psi |
| Tensile elongation | 2.4% |
| Distortion temperature under load | 184° F |
| Dielectric strength (perpendicular) | 513 volts/mil |
| Dissipation factor | |
| 60 cycles | 0.0022 |
| 1 megacycle | 0.0028 |
| Insulation resistivity | $2.5 \times 10^{13}$ ohms |
| Volume resistivity | $1.7 \times 10^{15}$ ohm-cm. |
| Surface resitivity | $3.8 \times 10^{15}$ ohms |
| Arc resistance | 97 seconds |

The value of the tensile elongation is of special interest since this is about optimum for use in filament winding techniques.

CHEMICAL RESISTANCE

The chemical resistance of Resin D was compared with that of a commercial resin (sold under the trade designation Altac 382 by Atlas Chemical Co.) having relatively good chemical resistance. It was found that both Resin D and the commercial resin had the same weight change (0.1%) after a 1-month immersion in a 10% NaOH solution at 99° C.

Other properties of Resin D were determined as follows:

| Flexural strength | 13,700 psi |
|---|---|
| Flexural modulus | 448,000 psi |
| Tensile strength | 5,480 psi |
| Tensile modulus | 438,000 psi |
| Tensile elongation | 1.3% |

It is noted that in Examples I and II above, the ratio of styrene to butadiene monomer was selected in order to yield a polymer having an average sequence length of about 10 styrene units in each segment of the copolymer. This sequence length will vary as an inverse function of the amount of the butadiene monomer utilized in the copolymerization. While there is no particular criticality in the sequence length of the styrene units, a minimum of about five is thought necessary to obtain desirable results. On the other hand, it is not practical to attempt to obtain sequence lengths much greater than about 50 since to do so, requires that the butadiene monomer content be reduced to a point at which the yield of copolymer is diminished with an accompanying increase in the yield of vinyl homopolymer.

We claim:
1. Low molecular weight vinyl polymers having chain terminating reactive groups having the general formula

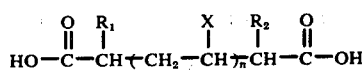

in which
R₁ is hydrogen, lower alkyl having 1 to 4 carbon atoms, or halogen;
R₂ is hydrogen, lower alkyl having 1 to 4 carbon atoms, or halogen;
X is aryl, free from ethylenic unsaturation and hydroxyl groups; and
n is from 5 to 50.

2. Low molecular weight vinyl polymers having chain terminating reactive groups having the general formula

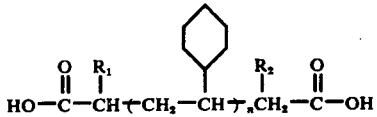

in which
R₁ is hydrogen, lower alkyl having 1 to 4 carbon atoms, or halogen;
R₂ is hydrogen, lower alkyl having 1 to 4 carbon atoms, or halogen; and
n is from 5 to 50.

3. A process for the preparation of low molecular weight vinyl polymers terminated with reactive end groups which comprises:
conducting a free radical polymerization of from about 83 mol.% to about 98 mol.% of an aryl substituted ethene with from about 17% to about 2% of a diene having the general formula:

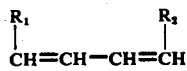

in which R₁ and R₂ are hydrogen, lower alkyl having 1 to 4 carbon atoms, or halogen;
collecting the solid polymer resulting from the polymerization and dissolving it in an anhydrous solvent which is inert to ozone; ;p1 ozonizing the dissolved polymer by introducing ozone into the solution; and
oxidizing to cleave the resulting ozonide to so form a low molecular weight vinyl polymer terminated on each of its ends with carboxylic acid end groups.

4. A process according to claim 3 wherein the aryl substituted ethene is styrene.

* * * * *